United States Patent

Snowden et al.

[11] Patent Number: 6,159,929
[45] Date of Patent: *Dec. 12, 2000

[54] OPTICALLY ACTIVE ESTERS AND THEIR USE AS PERFUMING INGREDIENTS

[75] Inventors: Roger L. Snowden, Viry, France; Hervé Pamingle, Versoix; Christian Vial, Geneva, both of Switzerland

[73] Assignee: Firmenich SA, Geneva, Switzerland

[*] Notice: This patent is subject to a terminal disclaimer.

[21] Appl. No.: 09/339,941

[22] Filed: Jun. 25, 1999

Related U.S. Application Data

[63] Continuation-in-part of application No. 09/204,966, Dec. 3, 1998, Pat. No. 5,952,292.

[30] Foreign Application Priority Data

Dec. 8, 1997 [CH] Switzerland .......................... 2825/97

[51] Int. Cl.[7] .............................. A61K 7/46; A61K 6/00; A61K 7/00; A61L 9/04
[52] U.S. Cl. .................................. 512/26; 512/1; 512/25; 512/27; 424/401; 424/76.4
[58] Field of Search .................................. 512/1, 25, 26, 512/27; 424/401, 76.4

[56] References Cited

FOREIGN PATENT DOCUMENTS

WO 96/10927   4/1996   WIPO .

OTHER PUBLICATIONS

R. Kozlowski et al., "Lower Aliphatic 2–Oxoacids and their Ethyl Esters From Ethyl Esters of 2–Hydroxy Acids", Organic Preparations and Procedures Inc. 21(1), 75–82 (1989).

Y. Akiyama et al., "Studies on Conjugated Nitriles. IV.", Chem. Pharm. Bull. 32 (5) 1800–1807 (1984).

Y. Akiyama et al., "Reaction of Organocadmium Reagents with Ethyl Cyanoformate: preparation of α–Keto Esters", Chemistry Letters, pp. 1231–1232, 1983.

P. Yates et al., "Synthesis of piperazine–2,5–diones related to bicyclomycin; 1,4–dibenzyl–3–hydroxy–3–[1–(2–methoxyethyl) ethenyl] piperzaine–2,5–dione, 2. Route via cyclic intermediates". Can. J. Chem. 61970, 1397–1404 (1983).

H.M. Walborsky, "Partial Asymmetric Syntheses of Amino Acids Using Lithium Aldimine Precursors", J. Org. Chem., vol. 39, (5), 604–607, 1974.

L.N. Akimova. "Preparation of Estes of α–Keto Acids by the Actions of Grignard Reagents of Oxalic Esters". Zhurnal Organicheskoi Khimii 5(9) pp. 1569–1571, Sep. 1969.

Kaiser, "New Volatile Constituents of the Flower Concrete of *Michelia champaca* L.", *J. Ess. Oil Res.*, 3:129–146 (May/Jun. 1991).

Kozlowski et al., "Lower Aliphatic 2–Oxoacids and Their Ethyl Esters From Ethyl Esters of 2–Hydroxy Acids", *Org. Prep. Proceed. Int.*, 21:75–82 (1989).

Wistuba et al., "Enantio– and Regioselectivity in the Epoxide–Hydrolase–Catalyzed Ring Opening of Aliphatic Oxiranes: Part II: Dialkyl– and Trialkylsubstituted Oxiranes", *Chirality*, 4:185–192 (1992).

*Primary Examiner*—Jill Warden
*Assistant Examiner*—Monique T. Cole
*Attorney, Agent, or Firm*—Pennie & Edmonds LLP

[57] ABSTRACT

A compound of formula

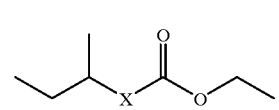

(I)

wherein X represents a C=O group or a CH—OH group, in the form of an optically active isomer of formula

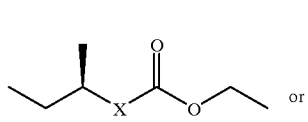

(Ia)

or

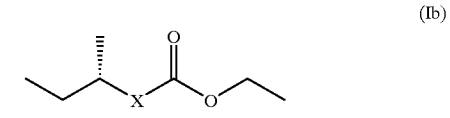

(Ib)

wherein X has the meaning indicated above and, when X is a CH—OH group, the asymmetric carbon (2) has an R configuration, or in the form of a mixture of isomers, is very useful in the field of perfumery, having an unusual, fruity odor note that can be described as a fresh walnut odor together with a rhum type note.

14 Claims, No Drawings

OPTICALLY ACTIVE ESTERS AND THEIR USE AS PERFUMING INGREDIENTS

This application is a continuation-in-part of U.S. Ser. No. 09/204,966 filed on Dec. 3, 1998 now U.S. Pat. No. 5,952,292, issue date Sep. 14, 1999.

BRIEF SUMMARY OF THE INVENTION

The invention belongs to the field of perfumery. It relates more particularly to a compound of formula

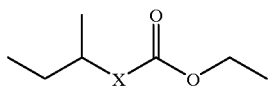
(I)

wherein X represents a C=O group or a CH—OH group, in the form of an optically active isomer or of a mixture of isomers, and its use as a perfuming ingredient.

BACKGROUND OF THE INVENTION

The structure of the esters of formula (I) in racemic form is known. Several references have disclosed it, either mentioning only the molecule, or describing its preparation in detail. In this context, the following references can be cited for their mention of the compound of formula (I) wherein X represents a C=O group, namely 3-methyl-2-oxo-ethyl pentanoate: R. Kozlowski et al., Org. Prep. Proceed. Int., 21(1), 75–82 (1989); Y. Akiyama et al., Chem. Pharm. Bull. 32(5), 1800–1807 (1984); Y. Akiyama et al., Chem. Lett. 8, 1231–1232 (1983); P. Yates et al., Can. J. Chem. 61(7), 1397–1404 (1983); H. M. Walborsky et al., J. Org. Chem. 39(5), 604–607 (1974); L. N. Akimova et al., Zh Org. Khim. 5(9), 1569–1571 (1969). However none of these references either describes the odor of said ester or suggests its utilization in the field of perfumery.

Moreover, the acids of formula

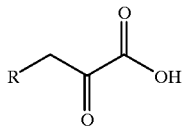
(II)

wherein R can be hydrogen or represents a great variety of alkyl radicals, saturated or unsaturated, linear or branched, and namely 3-methyl-2-oxopentanoic acid, are known to be used in the field of flavors. The international application WO 96/10927 describes the utilization of this group of compounds in a variety of foods, to which they impart an enhanced impact in the mouth. The $C_1$ to $C_4$ alkyl esters of said acids are also mentioned as useful flavoring ingredients in a general manner, without however giving any concrete example of preparation or even of application of these alkyl esters. Once again there is no description of the odor characteristics of said esters.

On the other hand, the racemic compound of formula (I) wherein X represents a CH—OH group, namely ethyl 2-hydroxy-3-methylpentanoate is described in the following articles: R. Kaiser, J. Ess. Oil Res. (1991), 3, 129–146 or R. Kozlowski, Z. Kubica, B. Rzeszotarska, L. Smelka, G. Pietrzynski, Org. Prep. Proced. Int. (1989), 21(1), 75–82. Moreover, the synthesis of one of the four optically active isomers of this compound, namely ethyl (2S,3S)-2-hydroxy-3-methylpentanoate has been described by D. Wistuba, O. Träger and V. Schurig in Chirality (1992), 4(3), 185–92. However, this article does not include any description of the organoleptic properties of said isomer and generally speaking, the prior art never suggests any possible usefulness of the isomers of 2-hydroxy-3-methyl-pentanoate from an olfactory point of view.

DETAILED DESCRIPTION OF THE INVENTION

Surprisingly, we have now been able to establish that the esters of formula (I) in the form of an optically active isomer or of a mixture of isomers, are very useful perfuming ingredients, having an original and unusual odor, which is a combination of fresh and fruity notes with a walnut type odor character.

The invention is thus related to a method to confer, improve, enhance or modify the odor properties of a perfuming composition or a perfumed product, which method comprises adding as perfuming ingredient to said composition or product, a compound of formula

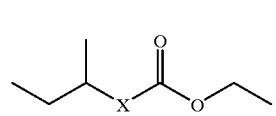
(I)

wherein X represents a C=O group or a CH—OH group, in the form of an optically active isomer of formula

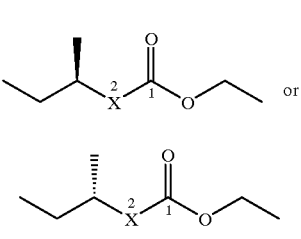
(Ia)

or (Ib)

wherein X has the meaning indicated above and when X is a CH—OH group, the asymmetric carbon (2) has an R configuration, or in the form of a mixture of isomers.

More particularly, the esters of the invention present a complex odor note of the walnut type, that can be described as being reminiscent of the odor of a fresh walnut, together with a walnut husk character. This note is surprisingly fruity; moreover, there is also a hazelnut connotation. The characteristic walnut-fresh hazelnut note is accompanied by an odor which is reminiscent of that of rhum. In sum, the odor is very natural, of an excellent and unusual quality.

The compound of formula (I) wherein X represents a C=O group, in the form of a racemic mixture, namely 3-methyl-2-oxo-ethyl-pentanoate, brings a new odor note to the perfumer's palette, a fruity, walnut note which is very natural and which was not available until today. This unusual combination of a fruity connotation with a very natural walnut-rhum odor renders this compound of the invention of great value for use in perfumery.

Each of its optically active isomers has distinct odor properties. Thus (+)-ethyl-(S)-3-methyl-2-oxopentanoate presents a typical walnut note, accompanied by a walnut-husk, pungent, etheral, slightly fruity odor, while (−)-ethyl-(R)-3-methyl-2-oxopentanoate also has a typical walnut note, but its odor is more pungent, more dry, less powerful and does not posses the fruity-apple note.

The compound of formula (I) wherein X represents a CH—OH group is particularly interesting from an olfactory point of view, particularly when in the form of an optically active isomer of formula (Ia) or (Ib) as defined above. In fact, while the odor of the racemate has a top note reminiscent of camphor together with earthy and slightly fruity notes, the isomers fragrances present top notes of the walnut type, but with distinct nuances. In the case of the compound (Ib), the odor is more oily with a bottom note typical of the odor of apple. The other isomer (Ia) is preferred according to the invention for its walnut note accompanied by a pleasant connotation typical of fenugreek and nussol.

The compounds of the invention are particularly useful in fine perfumery, namely in the creation of perfumes, colognes or after-shave lotions.

However, it goes without saying that their utilization is not limited to the above-mentioned products, and these compounds can suit any other usual application in perfumery, namely to perfume soaps and shower or bath gels, hygiene or hair care products such as shampoos and also body or ambient air deodorants and cosmetic preparations.

The compounds can also be used in applications such as liquid or solid detergents for textile treatment, fabric softeners, or yet detergent compositions or cleaning products for dishes or varied surfaces, for a domestic as well as an industrial use.

In these applications, said compounds (I) can be used alone as well as mixed with other perfuming ingredients, solvents or additives commonly used in perfumery. The nature and variety of these coingredients do not require a more detailed description here, which would not be exhaustive anyway. In fact, a person skilled in the art, having a general knowledge, is able to choose them according to the nature of the product that has to be perfumed and the olfactory effect sought. These perfuming coingredients belong to varied chemical groups such as alcohols, aldehydes, ketones, esters, acetates, nitrites, terpenic hydrocarbons, heterocyclic nitrogen- or sulfur-containing compounds, as well as natural or synthetic essential oils. Many of these ingredients are listed in reference texts such as S. Arctander, Perfume and Flavor Chemicals, 1969, Montclair, N.J., USA, or more recent versions thereof, or in other similar books.

The proportions in which the compounds according to the invention can be incorporated in the different products mentioned above vary in a broad range of values. These values depend on the nature of the product that has to be perfumed and on the olfactory effect sought, as well as on the nature of the coingredients in a given composition when the compounds of the invention are used in admixture with perfuming coingredients, solvents or additives commonly used in the art.

For instance, concentrations from 0.1 to 10% by weight of these compounds with respect to the weight of the perfuming composition in which they are incorporated, can be used. Much lower concentrations than these can typically be used when these compounds are directly applied for perfuming some of the consumer products mentioned above.

The invention also relates to a process for the preparation of each of the optically active esters of the invention, which are novel compounds. Therefore, ethyl (2R,3R)-2-hydroxy-3-methylpentanoate and ethyl (2R,3S)-2-hydroxy-3-methylpentanoate are synthesized respectively from (−)-(2R,3R)-D-isoleucine and (−)-(2R,3S) -D-allo-isoleucine which are converted into the corresponding hydroxyacids in the first step, with retention of the configuration and then, into the desired hydroxyesters of formula (Ia) and (Ib) wherein X represents a CH—OH group, via an esterification.

The keto-esters of formula (Ia) and (Ib) (wherein X is a C=O group) are synthesized in three steps, starting respectively from (+)-(2S,3R)-L-allo-isoleucine and (+)-(2S,3S)-isoleucine. The two first steps are similar to the preparation of the hydroxyesters described above and the third step is carried out by adding successively sodium acetate and pyridinium chlorochromate to a solution of ethyl (2S,3R)-2-hydroxy-3-methylpentanoate, respectively ethyl (2S,3S)-2-hydroxy-3-methyl-pentanoate. These synthesis will be described in more detail in the examples presented further on.

The invention will now be described in greater detail in the following examples, wherein the temperatures are indicated in degrees centigrade and the abbreviations have the usual meaning in the art.

EXAMPLE 1

Preparation of the Optically Active Isomers According to the Invention

1. Synthesis of (+)-ethyl-(S)-3-methyl-2-oxopentanoate

The synthesis was carried out in three steps, according to the following scheme:

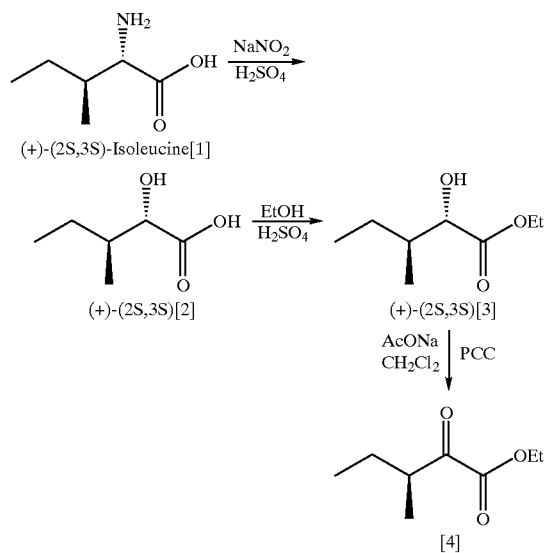

1.1. Synthesis of(+)-(2S, 3S)-2-hydroxy-3-methylpentanoic acid [2]

To a solution of (+)-L-isoleucine [1] (11.73 g, 89.4 mmol, $[\alpha]^D{}_{20}$=+40° (5% in 6M HCl)) in 300 ml of 1N aq. $H_2SO_4$ at 2° was slowly added (ca. 12 h) a solution of $NaNO_2$ (19.5 g, 0.28 mol) in 300 ml of demineralised water. After stirring overnight at room temperature, 7.7 g of powdered $NaHCO_3$ were added to bring the pH above 2. The solution was saturated with NaCl and extracted 6 times with ethyl acetate, maintaining the pH between 2 and 3 (1N aq. $H_2SO_4$, pH meter). After drying ($Na_2SO_4$), the organic layer was concentrated and the crude product (10.73 g, 91%) was recrystallised from hexane/ethyl acetate 9/1at −30° to give pure (+)-(2S,3S)-2-hydroxy-3-methylpentanoic acid [2].

Analytical data:

m.p.=52–54°

$[\alpha]^P{}_{20}$=+22.4° (1.25% in CHCl$_3$)

MS: 132(M$^+$,0): m/e: 87(28), 76(100), 69(12), 57(25), 45(23), 29(14)

$^1$H-NMR(CDCl$_3$): 0.90(t, J=7, 3H); 0.98(d, J=7, 3H); 1.26(m, 1H); 1.41(m, 1H); 1.83(m, 1H); 4.13(d, J$_1$=4)

$^{13}$C-NMR(CDCl$_3$): 2q: 11.7, 15.2; 1t: 23.8; 2d: 38.7, 74.7; 1s: 177.9

1.2. Synthesis of (+)-ethyl-(2S, 3S)-2-hydroxy-3-methylpentanoate [3]

To a solution of (+)-hydroxy acid [2] (4.57 g, 34.6 mmol) in 46 ml of absolute ethanol was added 0.3 g of conc. H$_2$SO$_4$ and the mixture was heated 5 h at 60°. After normal workup and concentration, the compound was distilled (bulb-to-bulb, 110–120°, 18×10$^2$ Pa) to give 4.65 g (yield: 84%) of 95.3% pure (+)-hydroxy ester [3]. A sample was purified by flash chromatography on SiO$_2$ (heptane/ether 65/35).

By GC analysis on a chiral column (CHIRASIL-DEX CB, 25 m×0.25 mm, isoth. 90°), the product was found to be enantiomerically pure (contained 2.5% of the 2R, 3S-diastereoisomer.

Analytical data:

$[\alpha]^P{}_{20}$=+16.7° (1.75% in CHCl$_3$)

MS: 160(M$^+$,1): m/e: 104(47), 87(95), 76(86), 69(38), 57(32), 45(100), 29(74)

$^1$H-NMR(CDCl$_3$): 0.90(t, J=7, 3H); 0.99(d, J=7, 3H); 1.30(t, J=7, 3H); 1.19–1.43(m, 2H); 1.81(m, 1H); 2.74 (d, J=6, 1H, disappear by add. of D$_2$O); 4.07(dd, J$_1$=4, J$_2$=6, 1H, collapse to d, J=4 by add. of D$_2$O); 4.26(m, 2H)

$^{13}$C-NMR(CDCl$_3$): 3q: 11.8, 14.2, 15.4; 2t: 23.8, 61.5; 2d: 39.1, 74.6; 1s: 175.0

1.3. Synthesis of (+)-ethyl-(S)-3-methyl-2-oxopentanoate [4]

To a solution of (+)-hydroxy ester [3] (2.0 g, 12.5 mmol) in 20 ml of CH$_2$Cl$_2$ at room temperature were added successively NaOAc (312 mg, 3.8 mmol) and PCC (pyridinium chlorochromate, 4.04 g, 18.75 mmol). After 24 h at room temperature, the conversion was only 60% and 2.02 g PCC were re-added. The mixture was stirred 96 h at room temperature, rapidly filtered on SiO$_2$, concentrated and purified by flash chromatography on SiO$_2$ to give 1.58 g of ester [4]. At this stage, a GC control on chiral column (CHIRASIL-DEX CB, 25 m×0.25 mm, isoth. 80°) showed a purity of 100% and an ee (enantiomeric excess) of 100%. After bulb-to-bulb distillation (Eb=100°, 16 mbars), 1.51 g (yield: 76.3%) of pure (+)-ester [4] were obtained.

Analytical data:

$[\alpha]^P{}_{20}$=+38.4° (0.7% in CHCl$_3$)

MS: 158(M$^+$,6): m/e: 102(4), 85(60), 69(3), 57(100), 41(25), 29(21)

$^1$H-NMR(CDCl$_3$): 0.92(t, J=7, 3H); 1.13(d, J=7, 3H); 1.38(t, J=7, 3H); 1.45(m, 1H); 1.77(m, 1H); 3.14(m, 1H); 4.32(q, J=7, 2H)

$^{13}$C-NMR(CDCl$_3$): 3q: 11.4, 14.1, 14.6; 2t: 25.0, 62.2; 1d: 43.6; 2s: 162.1, 198.3

2. Synthesis of (−)-ethyl-(R)-3-methyl-2-oxopentanoate

The synthesis was carried out in three steps, according to the following scheme:

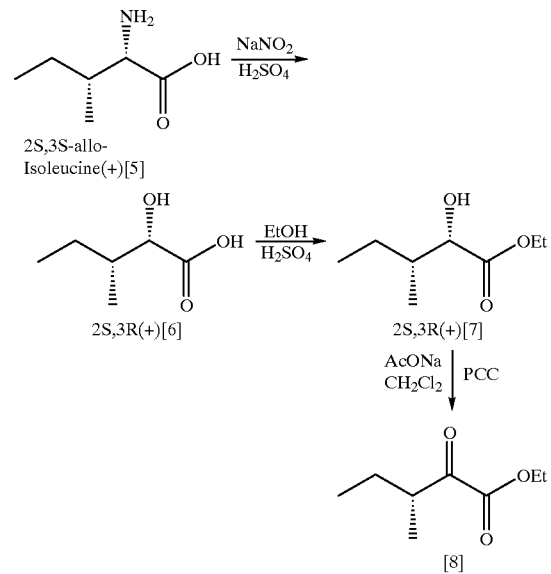

2.1. Synthesis of (+)-(2S, 3R)-2-hydroxy-3-methylpentanoic acid [6]

This compound was synthesised from (+)-L-allo isoleucine [5] ($[\alpha]^P{}_{20}$=+37° (5% in 6M HCl)) as described in 1.1. (yield: 93%).

Analytical data:

$[\alpha]^P{}_{20}$ =+18.7° (0.46% in CHCl$_3$)

MS: 132(M$^+$,0): m/e: 87(36), 76(100), 69(15), 57(28), 45(31), 29(19)

$^1$H-NMR(CDCl$_3$): 0.89(d, J=7, 3H); 0.97(t, J=7, 3H); 1.38(m, 1H); 1.54(m, 1H); 1.80(m, 1H); 4.30(d, J$_1$=3)

$^{13}$C-NMR(CDCl$_3$): 2q: 11.8, 13.1; 1t: 26.0; 2d: 38.3, 72.7; 1s: 178.9

2.2. Synthesis of (+)-ethyl-(2S, 3R)-2-hydroxy-3-methylpentanoate [7]

This compound has been synthesised from (+)-hydroxy acid [6] as described in 1.2. (yield: 66.4%).

Analytical data:

$[\alpha]^P{}_{20}$=+16.1° (0.91% in CHCl$_3$)

MS: 160(M$^+$,1): m/e: 104(38), 87(90), 76(70), 69(37), 57(32), 45(100), 29(70)

$^1$H-NMR(CDCl$_3$): 0.82(d, J=7, 3H); 0.96(t, J=7, 3H); 1.31(t, J=7, 3H); 1.34(m, 1H); 1.53(m, 1H); 1.81(m,1 H); 2.67(d, J=6, 1H, disappear by add. of D$_2$O); 4.18 (dd, J$_1$=3, J$_2$=6, 1H, collapse to d, J=3 by add. of D$_2$O); 4.26(m, 2H)

$^{13}$C-NMR(CDCl$_3$): 3q: 11.9, 13.1, 14.3; 2t: 26.0, 61.6; 2d: 38.5, 72.9; 1s: 175.4

2.3. Synthesis of (−)-ethyl-(R)-3-methyl-2-oxopentanoate [8]

This compound has been synthesised from (+)-hydroxy ester [7] as described in 1.3. (yield: 75%).

Analytical data:

$[\alpha]^P{}_{20}$=−36.1° (1.0% in CHCl$_3$)

MS, $^1$H-NMR and $^{13}$C-NMR were superimposable with those obtained for the (+)-isomer (see 1.3.).

3. Synthesis of ethyl (2R,3S)-2-hydroxy-3-methylpentanoate 3.1. Synthesis of (2R,3S)-2-hydroxy-3-methylpentanoic acid To a solution of (−)-D-allo-isoleucine [1.00 g, 7.634 mmol, $[\alpha]^P_{20}$=−37°(5% in 6M HCl)] in 26 ml of 1N aq. $H_2SO_4$ at 2° was slowly added (ca. 12 h) a solution of $NaNO_2$ (1.67 g, 24.13 mmol) in 26 ml of demineralised water. After stirring overnight at room temperature, 0.62 g of powdered NaHCO3 were added to bring the pH above 2. The solution was saturated with NaCl and extracted 6 times with ethyl acetate, maintaining the pH between 2 and 3 (1N aq. $H_2SO_4$, pH meter). After drying ($Na_2SO_4$), the organic layer was concentrated and the crude product (0.91 g, 91%) was directly used in the next step without further purification.

Analytical data:

$[\alpha]^P_{20}$=−19.90 (1.4% in $CHCl_3$)

MS: 132($M^+$,0): m/e: 87(36), 76(100), 69(15), 57(28), 45(31), 29(19)

$^1$H-NMR($CDCl_3$): 0.89(d, J=7, 3H); 0.97(t, J=7, 3H); 1.38(m, 1H); 1.54(m, 1H); 1.80(m, 1H); 4.30(d, J=3, 1H)

$^{13}$C-NMR($CDCl_3$): 2q: 11.8, 13.1; 1t: 26.0; 2d: 38.3, 72.7; 1s: 178.9

3.2. Synthesis of ethyl (2R,3S)-2-hydroxy-3-methylpentanoate

To a solution of the preceding hydroxy acid (0.85 g, 3.03 mmol) in 10 ml of abs. ethanol were added 80 mg of conc. $H_2SO_4$ and the mixture was maintained 4 h at room temperature. After normal workup and concentration, the compound was purified by flash chromatography on $SiO_2$ (heptane/ether 9/1) and distilled (bulb to bulb, 120°, 18×10$^2$ Pa) to give 0.60 g (58.3%) of pure ethyl (2R,3S)-2-hydroxy-3-methylpentanoate.

Analytical data:

$[\alpha]^P_{20}$=−14.8° (1.3% in $CHCl_3$)

MS: 160($M^+$,1): m/e: 104(48), 87(100), 76(53), 69(32), 57(18), 45(41), 29(16)

$^1$H-NMR($CDCl_3$): 0.82(d, J=7, 3H); 0.96(t, J=7, 3H); 1.31(t, J=7, 3H); 1.34(m, 1H); 1.53(m, 1H); 1.81(m, 1H); 2.67(d, J=6, 1H, disappear by add. of $D_2O$); 4.18(dd, $J_1$=3, $J_2$=6, 1H, collapse to d, J=3 by add. of $D_2O$); 4.26(m, 2H)

$^{13}$C-NMR($CDCl_3$): 3q: 11.9, 13.1, 14.3; 2t: 26.0, 61.6; 2d: 38.5, 72.9; 1s: 175.4

GC analysis on a chiral column (CHIRASIL-DEX CB, 25 m×0.25 mm, isoth. 90°) indicated that the product was contaminated by 1.9% of the (2S,2S) isomer.

4. Synthesis of ethyl (2R,3R)-2-hydroxy-3-methylpentanoate 4.1. Synthesis of (2R,3R)-2-hydroxy-3-methylpentanoic acid This compound was synthesized from (−)-D-isoleucine ($[\alpha]^P_{20}$=−36.8° (1% in 6M HCl) as described in 3.1. (yield: 84%).

Analytical data:

$[\alpha]^P_{20}$=−16.0° (0.97% in $CHCl_3$)

MS: 132($M^+$,0): m/e: 87(28), 76(100), 69(12), 57(25), 45(23), 29(14)

$^1$H-NMR($CDCl_3$): 0.90(t, J=7, 3H); 0.98(d, J=7, 3H); 1.26(m, 1H); 1.41(m, 1H); 1.83(m, 1H); 4.13(d, J=4, 1H)

$^{13}$C-NMR($CDCl_3$): 2q: 11.7, 15.2 ; 1t: 23.8; 2d: 38.7, 74.7; 1s: 177.9

4.2. Synthesis of ethyl (2R,3R)-2-hydroxy-3-methylpentanoate

This compound was synthesized from the preceding hydroxyacid as described in 3.2. (yield: 62.5%).

Analytical data:

$[\alpha]^P_{20}$ =−17.3° (0.9% in $CHCl_3$)

MS: 160($M^+$,1): m/e: 104(51), 87(100), 76(63), 69(31), 57(20), 45(56), 29(21) $^1$H-NMR($CDCl_3$): 0.90(t, J=7, 3H); 0.99(d, J=7, 3H); 1.30(t, J=7, 3H); 1.19–1.43(m, 2H); 1.81(m, 1H); 2.74(d, J=6, 1H, disappear by add. of $D_2O$); 4.07(dd, $J_1$=4, $J_2$=6, 1H, collapse to d, J=4 by add. of $D_2O$); 4.26(m, 2H)

$^{13}$C-NMR($CDCl_3$): 3q: 11.8, 14.2, 15.4; 2t: 23.8, 61.5; 2d: 39.1, 74.6; 1s: 175.0

GC analysis on a chiral column (CHIRASIL-DEX CB, 25 m×0.25 mm, isoth. 90°) indicated that the product was contaminated by 10% of the (2R,3S) isomer.

EXAMPLE 2

Perfuming Composition

A base perfiiming composition having a floral-fern (fougére) character was prepared by admixing the following ingredients:

Ingredients Parts by weight

| Ingredients | Parts by weight |
| --- | --- |
| Benzyl acetate | 170 |
| 3,5,5-Trimethylcyclohexanyl acetate | 20 |
| Tricyclo[5.2.1.0.(2,6)]dec-3-en-8-yl acetate | 20 |
| Citronellol | 40 |
| 10% Ethylvanilline* | 20 |
| Exolide ®[1)] | 140 |
| Heliotropine | 40 |
| Iralia ®[2)] | 100 |
| Lilial ®[3)] | 100 |
| Linalol | 120 |
| Phenylethanol | 40 |
| Amyl salicyclate | 40 |
| Benzyl salicyclate | 120 |
| Total | 970 |

*in dipropylene glycol
[1)]mixture of 1-oxacyclohexadecan-2-one and 1-oxa-(12,13)-cyclohexadecen-2-one; origin: Firmenich SA, Geneva, Switzerland
[2)]mixture of methylionone isomers; origin: Firmenich SA, Geneva, Switzerland
[3)]3-(4-tert-butylphenyl)-2-methylpropanal; origin: Givandan-Roure SA, Vernier, Switzerland When 30 parts by weight of 3-methyl-2-oxo-ethylpentanoate, or an isomer thereof, were added to this base perfuming composition, the latter acquired a superb fruity connotation, with a very natural, light walnut undernote. In this manner, a very natural sparkling aspect was imparted to the composition, which was highly appreciated. When 30 parts by weight of ethyl (2R,3R)-2-hydroxy-3-methylpentanoate were added to this base perfuming composition, the latter acquired a neat green walnut connotation, particularly fresh, with a slightly fenugreek-jasmine character and an undernote typical of green apple.

EXAMPLE 3

Perfuming Composition

A base perfuming composition having a rose-citrus character was prepared by admixing the following ingredients:

| Ingredients | Parts by weight |
| --- | --- |
| Dimethylbenzylcarbinyl acetate | 20 |
| Phenylethyl acetate | 30 |
| 10% Raspberry ketone | *5 |
| 10% **Cetalox ®[1] | 20 |
| Citronellol | 40 |
| Coumarine | 20 |
| Eugenol | 5 |
| Fructone ®[2] | 10 |
| Habanolide ®[3] | 120 |
| Hedione ®[4] | 100 |
| Iralia ®[5] | 60 |
| Lilial ®[6] | 35 |
| Lorysia ®[7] | 80 |
| Phenylhexanol | 140 |
| Hexyl Salicyclate | 60 |
| Tetrahydrolinalol | 120 |
| Verdox ®[8] | 30 |
| Vertofix Coeur[9] | 80 |
| Limonene[10] | 35 |
| Total | 1000 |

*in dipropylene glycol
**in 2-(2-ethoxyethoxy)-1-ethanol; origin: Firmenich SA, Geneva, Switzerland
[1] 8,12-epoxy-13,14,15,16-tetranorlabdane; origin: Firmenich SA, Geneva, Switzerland
[2] 2-methyl-1,3-dioxolane-2-ethyl acetate; origin: International Flavors & Fragrances, USA
[3] pentadecenolide; origin: Firmenich SA, Geneva, Switzerland
[4] methyl dihydrojasmonate; origin: Firmenich SA, Geneva, Switzerland
[5] see example 1
[6] see example 1
[7] 4-(1,1-dimethylethyl)-1-cyclohexyl acetate; origin: Firmenich SA, Geneva, Switzerland
[8] 2-tert-butyl-1-cyclohexyl acetate; origin: International Flavors & Fragrances, USA
[9] origin: International Flavors and Fragrances, USA
[10] origin: Firmenich SA, Geneva, Switzerland 30 Parts by weight of 3-methyl-2-oxo-ethyl-pentanoate, or an isomer thereof, were added to this floral base composition. A novel composition was thus obtained, having a fresher and more lifting connotation, thanks to the pleasant fruity note that the composition thus acquired.

30 parts by weight of ethyl (2R,3R)-2-hydroxy-3-methylpentanoate were added to this floral base composition. A novel composition was thus obtained, having a fresh and floral connotation the rosy nuance of which was reinforced by the fruity-walnut note typical of said compound of the invention. The composition had thus acquired a character typical of red-rose, ripe-rose.

What we claim is:

1. A method to confer, improve, enhance or modify the odor properties of a perfuming composition or a perfumed product, which method comprises adding as a perfuming ingredient to said composition or product, a compound of formula

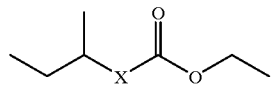
(I)

wherein X represents a C=O group or a CH—OH group, in the form of an optically active isomer of formula

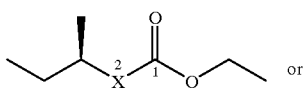
(Ia)

or

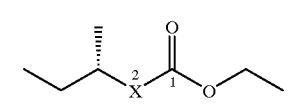
(Ib)

wherein X has the meaning indicated above and, when X is a CH—OH group, the asymmetric carbon (2) has an R configuration, or in the form of a mixture of isomers.

2. A perfuming composition or a perfumed product containing as active ingredient a compound of formula (I) as defined in claim 1.

3. Perfumed product according to claim 2, in the form of an after-shave lotion, a cosmetic preparation, a soap, a shampoo or hair-conditioner or another hair-care product, a bath or shower gel, a body or air deodorant, a detergent or a fabric softener, or a household product.

4. Perfumed product according to claim 2, in the form of a perfume or a cologne.

5. The method of claim 1 wherein X is a C=O group and the optically active isomer is of form (Ia).

6. The method of claim 1 wherein X is a C=O group and the optically active isomer is of form (Ib).

7. The method of claim 1 wherein X is a CH—OH group and the optically active isomer is of form (Ia).

8. The method of claim 1 wherein X is a CH—OH group and the optically active isomer is of form (Ib).

9. The method of claim 1 wherein the perfuming ingredient is added at a concentration of about 0.1 percent to about 10 percent by weight of the composition or product.

10. The perfuming composition of claim 2 wherein X is a C=O group and the optically active isomer is of form (Ia).

11. The perfuming composition of claim 2 wherein X is a C=O group and the optically active isomer is of form (Ib).

12. The perfuming composition of claim 2 wherein X is a CH—OH group and the optically active isomer is of form (Ia).

13. The perfuming composition of claim 2 wherein X is a CH—OH group and the optically active isomer is of form (Ib).

14. The active composition of claim 2 wherein the composition or product contains between about 0.1 percent and about 10 percent by weight of perfuming ingredient.

* * * * *